US008258353B2

(12) United States Patent  (10) Patent No.: US 8,258,353 B2
Kruper, Jr. et al.  (45) Date of Patent: Sep. 4, 2012

(54) PROCESS FOR THE PRODUCTION OF CHLORINATED AND/OR FLUORINATED PROPENES

(75) Inventors: William J. Kruper, Jr., Sanford, MI (US); Max M. Tirtowidjojo, Lake Jackson, TX (US); Kurt F. Hirsekorn, Midland, MI (US); Debashis Chakraborty, Lake Jackson, TX (US); Juergen Eiffler, Stade (DE)

(73) Assignee: Dow Global Technologies, LLC, Midland, MI (US)

( * ) Notice: Subject to any disclaimer, the term of this patent is extended or adjusted under 35 U.S.C. 154(b) by 0 days.

(21) Appl. No.: 12/799,170

(22) Filed: Apr. 20, 2010

(65) Prior Publication Data

US 2011/0178343 A1 Jul. 21, 2011

Related U.S. Application Data

(63) Continuation of application No. PCT/US2009/060101, filed on Oct. 9, 2009.

(51) Int. Cl.
C07C 17/266 (2006.01)
C07C 17/00 (2006.01)
(52) U.S. Cl. .................... 570/172; 570/155; 570/156
(58) Field of Classification Search .................. 570/155, 570/156, 172
See application file for complete search history.

(56) References Cited

U.S. PATENT DOCUMENTS

| | | |
|---|---|---|
| 2,119,484 A | 5/1938 | Levine et al. |
| 2,973,393 A | 2/1961 | Monroe |
| 3,446,859 A | 5/1969 | Weil et al. |
| 3,502,734 A | 3/1970 | Baird et al. |
| 3,651,019 A | 3/1972 | Asscher |
| 3,676,508 A | 7/1972 | Krekeler et al. |
| 3,819,731 A | 6/1974 | Pitt et al. |
| 3,823,195 A | 7/1974 | Smith |
| 3,872,664 A | 3/1975 | Lohmann et al. |
| 3,926,758 A | 12/1975 | Smith |
| 3,948,858 A * | 4/1976 | Wiersum ...................... 528/274 |
| 4,051,182 A | 9/1977 | Pitt |
| 4,513,154 A | 4/1985 | Kurtz |
| 4,535,194 A | 8/1985 | Woodard |
| 4,614,572 A | 9/1986 | Holbrook |
| 4,650,914 A | 3/1987 | Woodard |
| 4,702,809 A | 10/1987 | Mueller |
| 4,714,792 A | 12/1987 | Muller et al. |
| 4,716,255 A | 12/1987 | Muller |
| 4,726,686 A | 2/1988 | Wolf |
| 4,727,181 A | 2/1988 | Kruper |
| 4,894,205 A | 1/1990 | Westerman et al. |
| 4,902,393 A | 2/1990 | Muller |
| 5,057,634 A | 10/1991 | Webster |
| 5,132,473 A | 7/1992 | Furutaka et al. |
| 5,171,899 A | 12/1992 | Furutaka et al. |
| 5,254,771 A | 10/1993 | Cremer et al. |
| 5,315,044 A | 5/1994 | Furutaka et al. |
| 5,414,166 A | 5/1995 | Kim et al. |
| 5,684,219 A | 11/1997 | Boyce |
| 5,811,605 A | 9/1998 | Tang et al. |
| 5,895,825 A | 4/1999 | Elsheikh et al. |
| 6,111,150 A | 8/2000 | Sakyu et al. |
| 6,160,187 A | 12/2000 | Strickler et al. |
| 6,187,976 B1 | 2/2001 | Van der Puy et al. |
| 6,229,057 B1 | 5/2001 | Jackson et al. |
| 6,545,176 B1 | 4/2003 | Tsay et al. |
| 6,551,469 B1 | 4/2003 | Nair et al. |
| 6,610,177 B2 | 8/2003 | Tsay et al. |
| 6,825,383 B1 | 11/2004 | Dewkar et al. |
| 6,958,135 B1 | 10/2005 | Filippi et al. |
| 7,117,934 B2 | 10/2006 | Lomax et al. |
| 7,189,884 B2 | 3/2007 | Mukhopadhyay et al. |
| 7,226,567 B1 | 6/2007 | Olbert et al. |
| 7,282,120 B2 | 10/2007 | Braun et al. |
| 7,345,209 B2 | 3/2008 | Mukhopadhyay et al. |
| 7,371,904 B2 | 5/2008 | Ma et al. |
| 7,378,559 B2 | 5/2008 | Verwijs et al. |
| 7,511,101 B2 | 3/2009 | Nguyen et al. |
| 7,521,029 B2 | 4/2009 | Guetlhuber et al. |
| 7,588,739 B2 | 9/2009 | Sugiyama et al. |

(Continued)

FOREIGN PATENT DOCUMENTS

CN 101492341 7/2009
(Continued)

OTHER PUBLICATIONS

Nikishin et al., "Reactions of Methanol and Ethanol with Tetrachloroethylene", N.D. Zelinskii Institute of Organic Chemistry, Academy of Sciences of the USSR, Translated from Izvestiya Akademii Nauk SSSR, Seriya Khimicheskaya, No. 12, pp. 2188-2192, Dec. 1966.
Kruper et al., "Synthesis of alpha Halocinnamate Esters via Solvolytic Rearrangement of Trichloroallyl Alcohols", J. Org. Chem, 1991, pp. 3323-3329, 1991.
Boualy et al., "Kharasch addition of Tetrachloromethane to alkenes catalyzed by metal acetylacetonates", Catalysis Communications, 2011, 1295-1297, 12.
Cristiano et al., Tetraalkylphosphonium Trihalides. Room Temperature Ionic Liquids As Halogenation Reagents, J. Org. Chem., 2009, 9027-9033, 74.
Kruper et al., "Synthesis of alpha Halocinnamate Esters via Solvolytic Rearrangement of Trichloroallyl Alcohols", J. Org. Chem, 1991, pp. 3323-3329, 1991.
Boualy et al., "Kharasch addition of Tetrachloromethane to alkenes catalyzed by metal acetylacetonates", Catalysis Communications, 2011, 1295-1297, 12.

(Continued)

*Primary Examiner* — Jafar Parsa
(74) *Attorney, Agent, or Firm* — Lois K. Ruszala; KSJLaw, LLC

(57) ABSTRACT

The present invention provides one-step processes for the production of chlorinated and/or fluorinated propenes. The processes provide good product yield with low, e.g., less than about 20%, or even less than 10%, concentrations of residues/by-products. Advantageously, the processes may be conducted at low temperatures relative to conventional processes, so that energy savings are provided, and/or at higher pressures so that high throughputs may also be realized. The use of catalysts may provide enhancements to conversion rates and selectivity over those seen in conventional processes, as may adjustments to the molar ratio of the reactants.

10 Claims, 6 Drawing Sheets

U.S. PATENT DOCUMENTS

| | | | |
|---|---|---|---|
| 7,659,434 | B2 | 2/2010 | Mukhopadhyay et al. |
| 7,674,939 | B2 | 3/2010 | Mukhopadhyay et al. |
| 7,687,670 | B2 | 3/2010 | Nappa |
| 7,714,177 | B2 | 5/2010 | Mukhopadhyay et al. |
| 7,880,040 | B2 | 2/2011 | Mukhopadhyay et al. |
| 7,951,982 | B2 | 5/2011 | Mukhopadhyay et al. |
| 8,058,486 | B2 | 11/2011 | Merkel et al. |
| 8,115,038 | B2 | 2/2012 | Wilson et al. |
| 2006/0150445 | A1 | 7/2006 | Redding |
| 2006/0258891 | A1 | 11/2006 | Mukhopadhyay et al. |
| 2006/0292046 | A1 | 12/2006 | Fruchey |
| 2007/0112229 | A1 | 5/2007 | Mukhopadhyay et al. |
| 2007/0197841 | A1 | 8/2007 | Mukhopadhyay et al. |
| 2007/0197842 | A1 | 8/2007 | Mukhopadhyay et al. |
| 2007/0265368 | A1 | 11/2007 | Rao et al. |
| 2008/0118018 | A1 | 5/2008 | Schrauwen |
| 2008/0207962 | A1 | 8/2008 | Rao |
| 2009/0018377 | A1 | 1/2009 | Boyce |
| 2009/0030249 | A1 | 1/2009 | Merkel et al. |
| 2009/0099396 | A1 | 4/2009 | Mukhopadhyay et al. |
| 2009/0117014 | A1 | 5/2009 | Carpenter |
| 2009/0203945 | A1 | 8/2009 | Mukhopadhyay et al. |
| 2009/0253946 | A1 | 10/2009 | Van der Puy |
| 2009/0306438 | A1 | 12/2009 | Sievert et al. |
| 2010/0185029 | A1 | 7/2010 | Elsheikh et al. |
| 2010/0210883 | A1 | 8/2010 | Mukhopadhyay et al. |
| 2011/0218369 | A1 | 9/2011 | Elsheikh et al. |
| 2011/0251442 | A1 | 10/2011 | Okamoto |
| 2012/0035402 | A1 | 2/2012 | Wilson et al. |
| 2012/0065434 | A1 | 3/2012 | Nose et al. |

FOREIGN PATENT DOCUMENTS

| | | |
|---|---|---|
| CN | 101544535 | 9/2009 |
| CN | 101913979 | 12/2010 |
| CN | 101913980 | 12/2010 |
| CN | 101955414 A | 1/2011 |
| CN | 101982227 | 3/2011 |
| CN | 102249846 | 11/2011 |
| EP | 0131560 A1 | 1/1985 |
| EP | 1018366 A2 | 12/2000 |
| JP | 2001151708 | 6/2001 |
| JP | 2001213820 | 8/2001 |
| JP | 2007021396 A | 2/2007 |
| JP | 2008063314 | 3/2008 |
| JP | 2009046653 | 3/2009 |
| RU | 899523 | 1/1982 |
| WO | 0138275 | 5/2001 |
| WO | 2007079431 | 7/2007 |
| WO | 2007079435 | 7/2007 |
| WO | 2009003084 A1 | 12/2008 |
| WO | 2009067571 | 5/2009 |
| WO | 2009087423 | 7/2009 |
| WO | 2011060211 | 5/2011 |

OTHER PUBLICATIONS

Cristiano et al., Tetraalkylphosphonium Trihalides. Room Temperature Ionic Liquids As Halogenation Reagents, J. Org. Chem., 2009, 9027-9033, 74.

Evstigneev et al., "Initiated Chlorination of Tetrachloropropane", Khim. Prom., 1984, 393-394,16:7.

Ivanov et al., "Metal phthalocyanine-catalyzed addition of polychlorine-containing organic compounds to C=C bonds," Russian Chemical Bulletin, International Edition, 2009, 2393-2396 58(11).

Kharasch et al., "Chlorinations with Sulfuryl Chloride.I. The Peroxide-Catalyzed Chlorination of Hydrocarbons", J. Am. Chem. Soc., 1939, 2142-2150, 61.

Munoz-Molina et al., "An Efficient, Selective and Reducing Agent-Free Copper Catalyst for the Atom-Transfer Radical Addition of Halo Compounds to Activated Olefins", Inorg. Chem., 2010, 643-645, 49.

Nair et al., "Atom transfer radical addition (ATRA) of carbon tetrachloride and chlorinated esters to various olefins catalyzed by CP/Ru(PPh3)(PR3)CI complexes", Inorganica Chimica Acta, 2012, 96-103, 380.

Rotshtein et al., "Isomer Distribution on Chlorination of Chloropropanes", Z. Organicheskoi Khimii, 1966, 1539-1542, 2(9).

Semenov et al., "Selectivity of Photochemical Chlorination of Chloromethane in the Liquid Phase", Viniti, 1988, 3405-84.

Tanuma et al., "Partially Fluorinated Metal Oxide Catalysts for a Friedel-Crafts-type Reaction of Dichlorofluoromethane with Tetrafluoroethylene", Catal. Lett., 2010, 77-82, 136.

Ying et al., Isomerization of tetrachloropropene to promote utilization ration of triallate raw materials, Petrochemical Technology & Application, 2007, 25(1).

Zhao et al., "Research Progress on Preparation Technology of 1,1,2,3-Tetrachloropropene", Zhejiang Chemical Industry, vol. 41, No. 8 (2010).

Chai et al., "Study of Preparation of 1,1,13-Tetrachloropropane", Zhejiang Chemical Industry, 2010, 1-3, 41(5).

Dongfang et al., Review of the preparation of the low GWP alternative 1,3,3,3-Tetranuoropropene, Zhejiang Chemical Industry, 2010, 5-7, 41(3).

Huaping et al., "Process in the Synthesis of 1,1,1,3-Tetrachloropane", Guangzhou Chemicals, 2011, 41-43, 39(5).

Kang et al., "Kinetics of Synthesis of 1,1,1,3,3-pentachlorobutane catalyzed by Fe-FeCl3" Chemical Research and Application, Jun. 2011, 657-660, 23(6).

\* cited by examiner

PROCESS FOR THE PRODUCTION OF CHLORINATED AND/OR FLUORINATED PROPENES

CROSS REFERENCE TO RELATED APPLICATIONS

This application is a continuation of International Patent Application No. PCT/US09/60101, entitled "Process for the Production of Chlorinated and/or Fluorinated Propenes", filed Oct. 9, 2009, which is incorporated herein by reference.

FIELD

The present invention relates to processes for the production of chlorinated and/or fluorinated propenes.

BACKGROUND

Hydrofluorocarbon (HFC) products are widely utilized in many applications, including refrigeration, air conditioning, foam expansion, and as propellants for aerosol products including medical aerosol devices. Although HFC's have proven to be more climate friendly than the chlorofluorocarbon and hydrochlorofluorocarbon products that they replaced, it has now been discovered that they exhibit an appreciable global warming potential (GWP).

The search for more acceptable alternatives to current fluorocarbon products has led to the emergence of hydrofluoroolefin (HFO) products. Relative to their predecessors, HFOs are expected to exert less impact on the atmosphere in the form of a lesser detrimental impact on the ozone layer and their generally lower GWP. Advantageously, HFO's also exhibit low flammability and low toxicity.

As the environmental, and thus, economic importance of HFO's has developed, so has the demand for precursors utilized in their production. Many desirable HFO compounds, e.g., such as 2,3,3,3-tetrafluoroprop-1-ene (HFO-1234yf) or 1,3,3,3-tetrafluoroprop-1-ene (HFO-1234ze), may typically be produced utilizing feedstocks of chlorocarbons or chlorofluorocarbons, and in particular, chlorinated and/or fluorinated propenes.

Unfortunately, these chlorinated and/or fluorinated propenes may have limited commercial availability, and/or may only be available at potentially prohibitively high cost, due at least in part to the complicated, multi-step processes typically utilized in their manufacture. Furthermore, although simplified, one-step processes have been developed for the manufacture of chlorinated and/or fluorinated propenes, these processes have limited commercial applicability due to their limited throughput. Whether multi-step or one-step, many of the conventional manufacturing processes for the production of chlorinated and/or fluorinated propenes may typically result in the formation of large quantities of reaction by-products that must then be separated from the product and disposed of, typically at great expense, further limiting their commercial potential.

It would thus be desirable to provide improved processes for the production of chlorocarbon precursors useful in the synthesis of HFO's. More particularly, such processes would provide an improvement over the current state of the art if they were less costly not only in materials, but in time expenditure. Improvements in reaction productivity, selectivity and/or process throughput that could be provided without substantial detrimental impact on expense and/or safety concerns associated with the process would also provide commercial advantage.

BRIEF DESCRIPTION

The present invention provides such improved processes for the production of chlorinated and/or fluorinated propenes. Advantageously, the processes are one-step processes, thereby providing significant time, operating and capital cost savings over conventional multi-step processes for the production of chlorocarbon precursors for HFO's. Further, the processes provide good product yield with low, e.g., less than about 20%, or even less than about 10%, yield of residues/by-products, thus providing improvements over conventional one-step processes. The processes may be conducted at low temperatures relative to conventional processes, so that energy savings are provided, and/or at higher pressures so that high throughputs may be realized. The use of catalysts may provide enhancements to conversion rates and selectivity over those seen in conventional processes, as may the optimization of the molar ratio of the reactants.

More specifically, the processes comprise reacting a chloroethylene or a chlorofluoroethylene having the formula $CClX=CX_2$ where each X is independently Cl or F with a methane, chloromethane, fluoromethane, or chlorofluoromethane having the formula $CH_{4-a-b}Cl_aF_b$, wherein a is 0-3 and b is 0-3 at elevated pressures, i.e., pressures of greater than ambient, to provide at least one chlorinated and/or fluorinated propene. In some embodiments, the chlorinated and/or fluorinated propene may have the formula $CCl_cF_{2-c}=CCl_dF_{1-d}-CH_{3-e-f}Cl_eF_f$, wherein c is 0-2, d is 0-1, e is 0-3, and f is 0-3. One exemplary preferred reaction includes that wherein the chlorofluoroethylene comprises trifluorochloroethylene, the fluoromethane comprises methyl fluoride and the chlorinated and/or fluorinated propene comprises 1,1,2,3-tetrafluoropropene. Other exemplary preferred reactions include those wherein the chloroethylene comprises perchloroethylene. In such embodiments, the chloromethane may comprise methyl chloride, in which case the chlorinated and/or fluorinated propene comprises 1,1,2,3-tetrachloropropene, or the fluoromethane may comprise methyl fluoride, in which case the chlorinated and/or fluorinated propene comprises 1,1,2-chloro-3-fluoro-propene.

Desirably, the processes will be conducted at pressures of at least about 50 psig, or at least about 250 psig, or even at pressures of at least about 500 psig. The temperature of the processes may advantageously be lower than that of conventional processes, i.e., the temperature may be less than about 500° C., or less than about 450° C. or even less than about 400° C. Catalysts may be utilized in the process, and in those embodiments where the same is desired, free radical initiators, such as those comprising chlorine, e.g., carbon tetrachloride (Tet), hexachloroethane (HCE), benzotrichloride (BTC), hexachloroacetone (HCA), or chlorine, may be utilized. The ratio of $CH_{4-a-b}Cl_aF_b$ to $CClX=CX_2$ may advantageously be greater than 1, or greater than about 2.5. Combinations of one or more of elevated pressure, lower temperatures, the use of a catalyst, and the ratio of $CH_{4-a-b}Cl_aF_b$ to $CClX=CX_2$ may be utilized to provide further enhancements to the conversion rate, selectivity and/or cost savings provided by the process.

The processes described herein are expected to provide particular benefit when utilized to produce chlorinated and/or fluorinated propenes or higher alkenes, and in another aspect, the present invention so provides. The advantages provided by the present processes may be carried forward by utilizing the chlorinated and/or fluorinated propenes or higher alkenes to produce further downstream products, such as, e.g., 1,1,1,3-tetrafluoroprop-1-ene (HFO-1234ze) or 2,3,3,3-tetrafluoroprop-1-ene (HFO-1234yf).

BRIEF DESCRIPTION OF THE DRAWINGS

These and other features, aspects, and advantages of the present invention will become better understood when the following detailed description is read with reference to the accompanying drawings, wherein.

DETAILED DESCRIPTION

Figure 1:
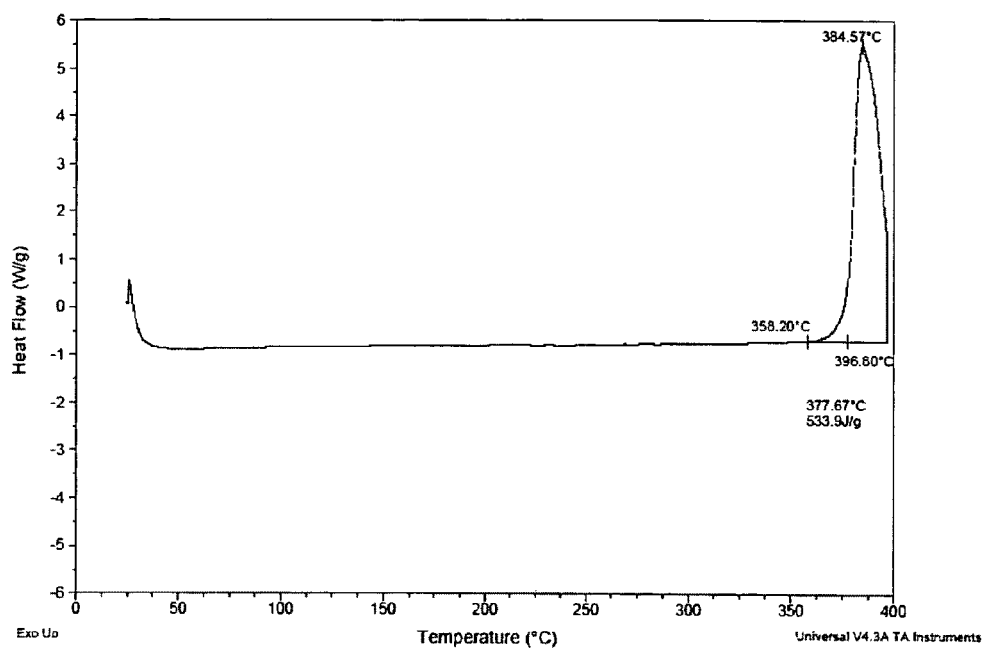
FIG. 1 is a graphical depiction of the results of the Differential Scanning Calorimetry (DSC) analysis of 1,1,2,3-tetrachloropropene.

The present specification provides certain definitions and methods to better define the present invention and to guide those of ordinary skill in the art in the practice of the present invention. Provision, or lack of the provision, of a definition for a particular term or phrase is not meant to bely any particular importance, or lack thereof. Rather, and unless otherwise noted, terms are to be understood according to conventional usage by those of ordinary skill in the relevant art.

The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced item, and the terms "front", "back", "bottom", and/or "top", unless otherwise noted, are merely used for convenience of description, and are not limited to any one position or spatial orientation.

If ranges are disclosed, the endpoints of all ranges directed to the same component or property are inclusive and independently combinable (e.g., ranges of "up to about 25 wt. %, or, more specifically, about 5 wt. % to about 20 wt. %," is inclusive of the endpoints and all intermediate values of the ranges of "about 5 wt. % to about 25 wt. %," etc.). The modifier "about" used in connection with a quantity is inclusive of the stated value and has the meaning dictated by the context (e.g., includes the degree of error associated with measurement of the particular quantity). As used herein, percent (%) conversion is meant to indicate change in molar or mass flow of reactant in a reactor in ratio to the incoming flow, while percent (%) selectivity means the change in molar flow rate of product in a reactor in ratio to the change of molar flow rate of a reactant.

"TCPE" is used as an abbreviation herein from time to time for 1,1,2,3-tetrachloropropene, "MeCl" is used as an abbreviation for methyl chloride, "Perc" is used as an abbreviation for perchloroethylene or tetrachloroethylene, "Tet" is used as an abbreviation for carbon tetrachloride, "BTC" is used as an abbreviation for benzotrichloride, "HCE" is used as an abbreviation for hexachloroethane, and "HCA" is used as an abbreviation for hexachloroacetone. Throughout the specification, the formula CClX=CX$_2$ wherein each X is independently Cl or F indicates the chloroethylene or chlorofluoroethylene as the case may be, while the formula CH$_{4-a-b}$Cl$_a$F$_b$, wherein a is 0-3 and b is 0-3 may be used to indicate the methane, chloromethane, fluoromethane or chlorofluoromethane. Finally, the formula CCl$_c$F$_{2-c}$=CCl$_d$F$_{1-d}$—CH$_{3-e-f}$Cl$_e$F$_f$ wherein c is 0-2, d is 0-1, e is 0-3, and f is 0-3, respectively, means the chlorinated and/or fluorinated propene(s).

The present invention provides improved processes for the production of chlorinated and/or fluorinated propenes. The present processes comprise only one step, the reaction of a chloroethylene or a chlorofluoroethylene with a methane, chloromethane, fluoromethane, or chlorofluoromethane thus, providing a significant time and materials savings over conventional processes. Additionally, the present processes may be carried out at lower temperatures than conventional processes, thus providing a cost savings, while yet also providing commercially acceptable throughputs not even achieved by the conventional high temperature processes.

Further, the present processes provide this good product yield while also providing low, e.g., less than about 20%, or even less than about 10% yield of residues/by-products, also an improvement over conventional one-step processes. The use of catalysts may provide further enhancements e.g., to conversion rates and selectivity, over those seen in conventional processes, as may the optimization of the molar ratio of the reactants.

Even though a one-step synthesis is a substantial improvement over conventional multi-step processes, in additional embodiments, one or more reaction conditions of the one step process may be optimized, in order to provide even further advantages, i.e., improvements in selectivity, conversion or production of reaction by-products. In certain embodiments, multiple reaction conditions are optimized and even further improvements in selectivity, conversion and production of reaction by-products produced can be seen.

Because of such improvements, the one-step process of the present invention may provide conversion rates of the methane, chloromethane, fluoromethane or chlorofluoromethane of at least about 1%, or about 2%, or about 5%, or up to about 10%, or in some instances, even up to about 15% or greater, without substantially reducing selectivity to the chlorinated and/or fluorinated propene. Conversion rates of the chloroethylene or chlorofluoroethylene of at least about 5%, or at least about 10%, or at least about 15%, or even up to about 20% or better can be seen, as can concentrations of impurities, such as redox impurities, of less than about 5 mole percent, less than about 2 mole percent, and in some embodiments, even less than 0.5 mole percent. The present processes also surprisingly provide selectivities to the chlorinated and/or fluorinated propene of at least about 50%, or up to about 60%, up to about 70%, up to about 80% when the chloroethylene or chlorofluoroethylene conversion is 30% or less, or up to about 90% when chloroethylene or chlorofluoroethylene conversion is 20% or less.

The chloroethylene or chlorofluoroethylene utilized in the present processes desirably have the formula CClX=CX$_2$ where each X is independently Cl or F. Suitable chloroethylenes or chlorofluoroethylenes do not comprise a hydrogen atom. Exemplary chloroethylenes and chlorofluoroethylenes that may be utilized in the present process thus include, but are not limited to 1-chloro-1,2,2-trifluoroethylene, 1,1-dichloro-2,2-difluoroethylene, 1,1,2-trichloro-2-fluoroethylene and 1,1,2,2-tetrachloroethylene, and cis-1,2-dichloro-1,2-difluoroethylene, and trans-1,2-dichloro-1,2-difluoroethylene.

The methane, chloromethane, fluoromethane or chlorofluoromethane utilized in the present processes desirably have the formula $CH_{4-a-b}Cl_aF_b$, wherein a is 0-3 and b is 0-3. Suitable chloromethanes, fluoromethanes and chlorofluoromethanes comprise at least one hydrogen atom. Thus, suitable chloromethanes, fluoromethanes and chlorofluoromethanes include, but are not limited to, methyl fluoride, methyl chloride, methylene fluoride, methylene chloride, chloroform and trifluoromethane, monochlorodifluoromethane, dichloromonofluoromethane, and monochloromonofluoromethane.

The present processes may advantageously be utilized to produce chlorinated and/or fluorinated propenes, in one step. In some embodiments, the chlorinated and/or fluorinated propenes that can be produced according to the present process include those having the formula $CCl_cF_{2-c}=CCl_dF_{1-d}-CH_{3-e-f}Cl_eF_f$ wherein c is 0-2, d is 0-1, e is 0-3, and f is 0-3. Examples of these include, but are not limited to, 1,1,2,3-tetrafluoropropene, 2,3,3,3-tetrafluoropropene, 1,1,2,3-tetrachloropropene, or 1,1,2-chloro-3-fluoro-propene.

Reaction conditions of the one-step process that may be optimized include any reaction condition conveniently adjusted, e.g., that may be adjusted via utilization of equipment and/or materials already present in the manufacturing footprint, or that may be obtained at low resource cost. Examples of such conditions may include, but are not limited to, adjustments to temperature, pressure, flow rates, molar ratios of reactants, use of catalysts or initiators, etc.

In one embodiment, reaction pressure is advantageously optimized, and may itself provide enhanced chlorinated and/or fluorinated propene selectivities relative to conventional processes, typically carried out at ambient pressures. More specifically, improvements to at least the chlorinated and/or fluorinated propene selectivity are expected at pressures of greater than about 15 psig, or greater than about 20 psig, or greater than about 35 psig, with improvement expected to increase with increase of pressure, up to about 200 psig, or up to about 300 psig, or up to about 400 psig, or even up to about 500 psig and greater. Optimizing at least pressure of the reaction in this fashion is estimated to provide selectivity to the chlorinated and/or fluorinated propene of at least about 50%, or up to about 60%, up to about 70%, and in some embodiments, up to about 80%.

The temperature of the reaction may also be optimized, and surprising results are expected when lowering the temperature, in particular when done in combination with pressure optimization. That is, although conventional processes typically call for temperatures of at least about 550° C., the present process may be carried out at less than 450° C., or less than about 400° C., or less than about 350° C., or even lower, while yet providing improvements to reactant conversions, product selectivity and lowering the capital cost associated with the use of the reactor.

The molar ratio of the reactants may also be optimized. While a 1:1 or lower ratio of the methane, chloromethane, fluoromethane or chlorofluoromethane to the chloroethylene or chlorofluoroethylene may be indicated in the art, a stoichiometric excess of the methane, chloromethane, fluoromethane or chlorofluoromethane may provide enhancements to the present process. More particularly, any molar ratio of $CH_{4-a-b}Cl_aF_b/CClX=CX_2$ in which $CH_{4-a-b}Cl_aF_b$ is present in excess may be utilized that is expected to result in enhancements to the process, whether in the form of increases to conversion or selectivity, or decreases in the production of impurities. Molar ratios of greater than about 1:1, or greater than about 2.0, or greater than about 2.5, or even greater than 5:1, may provide at least incremental improvements to the process. As with enhancements to temperature, any adjustments to the molar ratio may provide synergistic effects, but at least combinatorial enhancements, when utilized in conjunction with increases in reaction pressure.

Catalysts or initiators may also be utilized to enhance the present process. Surprisingly, the utilization of the same, in particular in conjunction with any of the other condition optimizations, does not result in an increase in the production of redox impurities by the process, but does provide selectivities to the chlorinated and/or fluorinated propene of at least about of at least about 50%, or up to about 60%, up to about 70%, and in some embodiments, up to about 80% or even higher.

Any catalyst or initiator capable of at least marginally enhancing the selectivity of the inventive process for the chlorinated and/or fluorinated propene may be utilized. Catalysts/initiators capable of doing so are believed to include those that are capable of removing hydrogen from methane, chloromethanes, fluoromethanes or chlorofluoromethanes to produce the corresponding radical. For example in the case of methyl chloride, the catalyst/initiators are capable for removing hydrogen from methyl chloride to form a chloromethyl radical, e.g., $*CH_2Cl$. Such free radical initiators are well known to those skilled in the art and have been reviewed, e.g., in "Aspects of some initiation and propagation processes," Bamford, Clement H. Univ. Liverpool, Liverpool, UK., Pure and Applied Chemistry, (1967), 15(3-4), 333-48 and Sheppard, C. S.; Mageli, I. L. "Peroxides and peroxy compounds, organic," Kirk-Othmer Encycl. Chem. Technol., 3rd Ed. (1982), 17, 27-90, both of which are hereby incorporated herein by reference in their entirety for any and all purposes.

Such catalysts may typically comprise one or more chlorine or peroxide groups and/or exhibit reactor phase mobility/activity. As used herein, the phrase "reactor phase mobility/activity" means that a substantial amount of the catalyst or initiator is available for generating free radicals of sufficient energy which can initiate and propagate effective turnover of the product, chlorinated and/or fluorinated propene, within the design limitations of the reactor.

Examples of suitable catalysts/initiators comprising chlorine include, but are not limited to carbon tetrachloride, chlorine, chloroform, hexachloroethane, phosgene, thionyl chloride, sulfuryl chloride, trichloromethylbenzene, perchlorinated alkylaryl functional groups, or organic and inorganic hypochlorites, including hypochlorous acid, and t-butylhypochlorite, methylhypochlorite, chlorinated amines (chloramine) and chlorinated amides or sulfonamides such as chloroamine-T®, and the like. Combinations of any of these may also be utilized.

Carbon tetrachloride ($CCl_4$), hexachloroethane, benzotrichloride and chlorine gas ($Cl_2$) are but a few examples that are readily commercially available and easily integrated into the present process, and their use can be preferred in embodiments wherein the use of a catalyst or initiator is desired.

Examples of suitable catalysts/initiators comprising one or more peroxide groups include hydrogen peroxide, hypochlorous acid, aliphatic and aromatic peroxides or hydroperoxides, including di-t-butyl peroxide, benzoyl peroxide, cumyl peroxide and the like.

In addition bis-azo initiators may have utility in effecting the addition of methane, chloromethane, fluoromethane or chlorofluoromethane to the chloroethylene or chlorofluoroethylene under the conditions of this invention.

In general, the catalyst/initiator should have sufficient homolytic dissociation energies such that the theoretical maximum of free radicals is generated from a given initiator under the temperature/residence time of the process. It is especially useful to use free radical initiators at concentrations where free radical chlorination of incipient radicals is prevented due to low concentration or reactivity. Diperoxides offer an advantage of not being able to propagate competitive processes (e.g., the free radical chlorination of methylchloride to methylene chloride).

Whatever the desired catalyst or initiator, those of ordinary skill in the art are well aware of methods of determining the appropriate concentration and method of introduction thereof. For example, many catalysts/initiators are typically introduced into the reactor zone as a separate feed, or in solution with other reactants, e.g., the chloroethylene or chlorofluoroethylene, which can be evaporated prior to the reaction zone. Also, initiators with a low boiling point can be introduced with inert gaseous diluents such as $N_2$.

The amount of any catalyst or initiator utilized will depend upon the particular catalyst/initiator chosen as well as the other reaction conditions. Generally speaking, in those embodiments of the invention wherein the utilization of a catalyst/initiator is desired, enough of the catalyst/initiator should be utilized to provide some improvement to reaction process conditions (e.g., a reduction in required temperature) or realized products, but yet not be more than will provide any additional benefit, if only for reasons of economic practicality. For purposes of illustration only, then, it is expected in those embodiments wherein a catalyst or initiator comprising carbon tetrachloride is desirably utilized, that useful concentrations thereof will range from about 5 ppm to about 200000 ppm, or from about 10 ppm to about 100000 ppm, or from about 20 ppm to about 50000 ppm, inclusive of all subranges therebetween.

The process can be further enhanced by subjecting the process or reactor zone to pulse laser or continuous UV/visible light sources at a wavelength suitable for inducing photolysis of the radical catalyst/initiator, as taught by Breslow, R. in *Organic Reaction Mechanisms* W.A. Benjamin Publ, New York p 223-224, hereby incorporated by reference herein in its entirety for any and all purposes. Wavelengths from about 300 to 700 nm of the light source are sufficient to dissociate commercially available radical initiators. Such light sources include, e.g., Hanovia UV discharge lamps, sunlamps or even pulsed laser beams of appropriate wavelength or energy which are configured to irradiate the reactor chamber. Alternatively, chloromethyl radicals may be generated from microwave discharge into a bromochloromethane feedsource introduced to the reactor as taught by Bailleux et al., in Journal of Molecular Spectroscopy, 2005, vol. 229, pp. 140-144, hereby incorporated by reference herein in its entirety for any and all purposes.

As mentioned above, the present invention provides improved processes for the production of chlorinated and/or fluorinated propenes, i.e., wherein one or more of the reaction conditions are optimized. In certain preferred embodiments, a lower temperature than that used conventionally is utilized in conjunction with an increased pressure to provide a process that results in a product stream with lower amounts of impurities. Conventional processes operate at much higher temperatures can suffer from excessive secondary decomposition of the desired chlorinated and/or fluorinated propene, which for some, is substantial at temperatures>400° C., lowering selectivity and process yield. FIG. 1 shows a DSC analysis of one exemplary chlorinated propene, 1,1,2,3-tetrachloropropene, and its adiabatic thermal decomposition onset at 365° C.

Even at short reactor contact time, 1,1,2,3-tetrachloropropene is unstable at 400° C.-500° C. and especially unstable at conventional reaction conditions (500° C.-750° C.). The ensuing decomposition leads to high concentrations of impurities, and ultimately thermal coking at these higher temperatures. For continuously fed, industrial reactors, coking is well known to cause further loss of selectivity with time and often requires shutting down a reactor for cleaning and maintenance.

By running at temperatures lower than those conventionally called for, not only are process cost savings provided, but lower capital costs are associated with the use of the reactor. And yet, in these embodiments of the invention, perchloroethylene conversions of at least about 5%, or at least about 10%, or at least about 15%, or even up to about 20% or even greater can be seen, along with $CH_{4-a-b}Cl_aF_b$ conversions of at least about 1%, or about 2%, or about 5%, or up to about 10%, or in some instances, even up to about 15% or greater and chlorinated and/or fluorinated propene selectivities of at least about 50%, or up to about 60%, up to about 70%, up to about 80% when conversion of the chloroethylene or chlorofluoroethylene is 30% or less, or up to about 90% when conversion of the chloroethylene or chlorofluoroethylene is 20% or less.

In an additional particularly preferred embodiment, higher pressure, i.e., greater than ambient, may be utilized in combination with an increased ratio (i.e., greater than 1) of $CH_{4-a-b}Cl_aF_b/CClX=CX_2$, a lowered temperature (i.e., lower than about 500° C.) and a catalyst/initiator to provide a process for the production of the chlorinated and/or fluorinated propene with expected chloroethylene or chlorofluoroethylene conversions of at least about 5%, or even 10%, as well as chlorinated and/or fluorinated propene selectivities of at least about 75%, or even 80%, 85%, or even up to 95% or greater. One particular such embodiment may utilize a reaction pressure of greater than about 25 psig, or, at least about 200 psig, or about 300 psig, or about 400 psig, a reaction temperature of lower than about 450° C., or lower than about 400° C., or even lower than about 350° C., a molar ratio of $CH_{4-a-b}Cl_aF_b/CClX=CX_2$ of greater than about 1.0, or greater than about 2.0, or greater than about 2.5, and a catalyst/initiator, e.g., such as those comprising chlorine, including but not limited to, chlorine gas, carbon tetrachloromethane, benzotrichloride, hexachloroacetone or hexachloroethane or combinations of these, in a concentration of from about 5 ppm to about 200000 ppm, or from about 10 ppm to about 100000 ppm, or from about 20 ppm to about 50000 ppm.

The present process may be conducted in any suitable reactor. Desirably, the reactor utilized will be one wherein the reaction conditions are readily and easily altered as desired, and also, that can function without damage or fouling at the selected conditions. These are expected to include near-isothermal shell and multitube reactors where the desired temperature can be achieved by means of utilization of a heat transfer field. Adiabatic cylindrical or tube reactors may also be used, and if used can have any desired length to diameter aspect ratio so long as preheating to the desired reaction temperature is possible. If an adiabatic reactor is utilized, a larger $CH_{4-a-b}Cl_aF_b$/chloroethylene or chlorofluoroethylene ratio, e.g., 3 or greater, or with the addition of a suitable diluents, such as inert diluents or $CH_{4-a-b}Cl_aF_b$ may be used in order to limit the adiabatic temperature rise, i.e., increase in temperature of less than 50° C., preferably from about 10° C.

to about 20° C. Alternatively, a series of adiabatic reactors with at least one intercooler operatively disposed relative thereto can also be employed to obtain the desired overall conversion while maintaining the desired temperature rise within each reactor.

The chlorinated and/or fluorinated propene produced by the present process may typically be processed to provide further downstream products including hydrofluoroolefins, such as, for example, 2,3,3,3-tetrafluoroprop-1-ene (HFO-1234yf) or 1,3,3,3-tetrafluoroprop-1-ene (HFO-1234ze). Since the present invention provides an improved process for the production of chlorinated and/or fluorinated propenes, it is contemplated that the improvements provided will carry forward to provide improvements to these downstream processes and/or products. Improved methods for the production of hydrofluoroolefins, 2,3,3,3-tetrafluoroprop-1-ene (HFO-1234yf) or 1,3,3,3-tetrafluoroprop-1-ene (HFO-1234ze), are thus also provided herein.

The conversion of chlorinated and/or fluorinated propenes to provide hydrofluoroolefins may broadly comprise a single reaction or two or more reactions involving fluorination of a compound of the formula $C(X)_m CCl(Y)_n(C)(X)_m$ to at least one compound of the formula $CF_3 CF=CHZ$, where each X, Y and Z is independently H, F, Cl, I or Br, and each m is independently 1, 2 or 3 and n is 0 or 1. A more specific example might involve a multi-step process wherein a feedstock of a chlorinated and/or fluorinated propene is fluorinated in a catalyzed, gas phase reaction to form a compound such as 2-chloro-3,3,3-tri-fluoropropene. The 2-chloro-2,3,3,3-tetrafluoropropane is then dehydrochlorinated to 2,3,3,3-tetrafluoropropene via a catalyzed, gas phase reaction.

The following examples are set forth for the purpose of illustrating the invention; but these examples are not intended to limit the invention in any manner. One skilled in the art will recognize a variety of substitutions and modifications of the examples that will fall within the scope of the invention. Particularly, even though the present description and examples refer with specificity to the reaction of $CH_{4-a-b}Cl_a F_b$ with chloroethylene or chlorofluoroethylene, the teachings herein, and advantages provided thereby, are expected to be readily and easily extrapolated by those of ordinary skill in the art to any free radical type reaction desirably conducted in the gas phase, and desirably employing chlorine radical catalyst/initiators.

Examples 1-8 below are hypothetical, i.e., reaction conditions were conceived of and further developed by the inventors of the present processes, and the expected results of these optimized parameters/conditions confirmed via computer simulation. The ranges of relative error associated with the perchloroethylene conversions are expected to be in the 30% range and the 1,1,2,3-tetrachloropropene relative error in the range of less than 20%.

EXAMPLE I

Impact of the Combination of Increased Molar Ratio of MeCl to Perchloroethylene and Increased Pressure on the Production of 1,1,2,3-tetrachloropropene A flow of 200 sccm of Perc will be established through a glass tube reactor (¾" inner diameter, 40" in length) packed with glass beads having a porosity of 0.35 (ratio of void volume of the reactor filled with glass beads to reactor volume without glass beads). The temperature within the reactor and that of the reactants (mixed at the entrance of the reactor) will be adjusted to achieve isothermal conditions of about 548° C. Flow to the reactor will be adjusted to provide a molar ratio of MeCl/Perc of at least about 0.75 at substantially ambient pressure and the reaction allowed to proceed for at least about 3 seconds. Then, the molar ratio of MeCl/Perc will be adjusted to about 2.5 and the pressure increased to about 7 psig, and the reaction allowed to proceed for at least about 5 seconds. Finally, the MeCl/Perc ratio will be adjusted to about 6 and the pressure increased to at least about 35 psig. Estimated MeCl and Perc conversions and % selectivity to TCPE are shown below in Table 1.

TABLE 1

Estimated Effect of Increasing MeCl/Perc Ratio and Pressure

|  | Pressure (psig) | | |
| --- | --- | --- | --- |
|  | 0 | 7 | 35 |
| Temperature (° C.) | 548 | 450 | 400 |
| SCCM Perc flow rate | 200 | 200 | 200 |
| MeCl/Perc molar ratio | 0.75 | 2.5 | 6 |
| % Perc conversion | 12.5 | 19.4 | 30 |
| % MeCl conversion | 16.1 | 8.29 | 5.8 |
| % TCPE selectivity | 54.5 | 57.5 | 58.3 |

As shown in Table 1, increased yield of TCPE is expected when the MeCl/Perc molar ratio and pressure are increased simultaneously. Taken alone, an increase in the MeCl/Perc ratio is expected to improve the selectivity to TCPE, while an increase in pressure is expected to increase the conversion of Perc.

EXAMPLE II

Impact of the Combination of Lowered Temperature and Increased Pressure on the Production of 1,1,2,3-tetrachloropropene A flow of 200 sccm of Perc will be established through a glass tube reactor (¾" inner diameter, 40" in length) packed with glass beads having a porosity of 0.35. The initial temperature within the reactor and that of the reactants (mixed at the entrance of the reactor) will be adjusted to achieve isothermal conditions of about 548° C. and the pressure adjusted to be about 7 psig. The flow will be adjusted to provide a molar ratio of MeCl/Perc of about 2.5 and the reaction allowed to proceed for at least about 3 seconds, at which time the temperature will be decreased to about 450° C. and the pressure increased to about 200 psig. The reaction will be allowed to proceed at these conditions for at least about 52 seconds. Then, the temperature will again be decreased to about 400° C. Estimated MeCl and Perc conversions and % selectivity to TCPE are shown below in Table 2.

TABLE 2

Estimated Effect of Increasing Pressure and Lowering Temperature on the production of TCPE

|  | Pressure (psig) | | |
| --- | --- | --- | --- |
|  | 7 | 200 | 1200 |
| Temperature (° C.) | 548 | 450 | 400 |
| SCCM Perc flow rate | 200 | 200 | 200 |

TABLE 2-continued

Estimated Effect of Increasing Pressure and Lowering Temperature on the production of TCPE

| | Pressure (psig) | | |
|---|---|---|---|
| | 7 | 200 | 1200 |
| MeCl/Perc molar ratio | 2.5 | 2.5 | 2.5 |
| % Perc conversion | 19.4 | 31.07 | 40.31 |
| % MeCl Conversion | 8.29 | 13.36 | 17.11 |
| % TCPE selectivity | 57.5 | 69.89 | 75.93 |

As shown, lowering temperature while increasing reactor pressure is expected to provide a beneficial impact on per-pass yield. Also under these conditions, it is expected to be possible to increase both the conversion of MeCl and Perc, while lowering the recycle rate of either reactant and thus lowering the capital cost of operating the reactor.

EXAMPLE III

Impact of the Use of an Catalyst/Initiator and Elevated Pressure on the Production of TCPE A flow of 200 sccm of Perc will be established through a glass lined tube reactor (¾" inner diameter, 40" in length) packed with glass beads having a porosity of 0.35. The initial temperature within the reactor and that of the reactants (mixed at the entrance of the reactor), will be adjusted to achieve isothermal conditions of about 548° C. and the pressure adjusted to be about 1200 psig. The flow will be adjusted to provide a molar ratio of MeCl/Perc of about 2.5 and to include an amount of an initiator, either $CCl_4$ or $Cl_2$. The reaction will be allowed to proceed for at least about 5.3 minutes, at which time the pressure will be decreased to about 700 psig. The reaction will be allowed to proceed at these conditions for at least about 3.1 minutes. Estimated MeCl and Perc conversions and % selectivity to TCPE are shown below in Table 3.

TABLE 3

Estimated Effect of Adding Initiator and Lowering Temperature

| | Pressure (psig) | | | | |
|---|---|---|---|---|---|
| | 1200 | 700 | 700 | 700 | 700 |
| Temperature (° C.) | 548 | 548 | 548 | 548 | 548 |
| SCCM Perc flow rate | 200 | 200 | 200 | 200 | 200 |
| MeCl/Perc molar ratio | 2.5 | 2.5 | 2.5 | 2.5 | 2.5 |
| Initiator | None | $CCl_4$ | $CCl_4$ | $CCl_4$ | $Cl_2$ |
| mole % initiator | 0 | 3.56E−02 | 3.56E−03 | 3.56E−01 | 3.56E−02 |
| % Perc conversion | 40.31 | 39.71 | 35.10 | 47.52 | 34.66 |
| % MeCl conversion | 17.11 | 14.76 | 14.61 | 20.64 | 14.61 |
| % TCPE selectivity | 75.93 | 75.95 | 77.12 | 73.50 | 78.56 |

As shown, the use of $CCl_4$ initiator is expected to reduce the required pressure significantly for achieving the same yield. More specifically, concentrations of about 30-40 ppm $CCl_4$ initiator are expected to provide slightly lower conversion and yield with a slight improvement in selectivity. At 300-4000 ppm concentrations of $CCl_4$, higher Perc conversions are expected with a slight reduction in the TCPE selectivity. At the same concentrations, $Cl_2$ is expected to provide similar catalytic effect with perhaps a slightly lower Perc conversion.

EXAMPLE IV

Impact of the Use of an Initiator, Lowered Temperature, Increased Pressure and Increased MeCl/Perc Molar Ratio on the Production of TCPE A flow of 200 sccm of Perc will be established through a glass lined tube reactor (¾" inner diameter, 40" in length) packed with glass beads having a porosity of 0.35. Initially, the pressure within the reactor will be ambient and the temperature within the reactor adjusted to achieve isothermal conditions of about 548° C. The flow will be adjusted to provide a molar ratio of MeCl/Perc of about 0.75 with no initiator. The reaction will be allowed to proceed under these conditions for at least about 3 seconds. Then, the temperature will be lowered to about 350° C., the pressure increased to about 700 psig, the MeCl/Perc molar ratio increased to about 2.5 and $CCl_4$ initiator introduced at a concentration of from about 3000-4000 ppm. The reaction will be allowed to proceed at these conditions for at least about 3.4 minutes. Estimated MeCl and Perc conversions and % selectivity to TCPE are shown below in Table 4.

TABLE 4

Estimated Effect of Increased Pressure, Lowered Temperature and Initiator

| | Pressure (psig) | |
|---|---|---|
| | 0 | 700 |
| $CCl_4$ mole % | 0 | 0.356 |
| Temperature (° C.) | 548 | 350 |
| MeCl/Perc molar ratio | 0.75 | 2.5 |
| % Perc Conversion | 12.5 | 12.3 |
| % TCPE selectivity | 54.5 | 86.3 |

As shown, it is expected that the highest selectivity to TCPE at the same conversion will be achieved by simultaneously increasing pressure, lowering temperature, using initiator and using a larger MeCl/Perc molar ratio than about 0.75.

EXAMPLE V

Impact of the Combination of Increased Molar Ratio of $CH_{4-a-b}Cl_aF_b$ to Chloroethylene or Chlorofluoroethylene and Increased Pressure on the Production of Chlorinated and/or Fluorinated Propenes A flow of 200 sccm of a chloroethylene or chlorofluoroethylene will be established through a glass tube reactor (¾" inner diameter, 40" in length) packed with glass beads having a porosity of 0.35 (ratio of void volume of the reactor filled with glass beads to reactor volume without glass beads). The temperature within the reactor and that of the reactants (mixed at the entrance of the reactor) will be adjusted to achieve isothermal conditions of about 548° C. Flow to the reactor will be adjusted to provide a molar ratio of $CH_{4-a-b}Cl_aF_b$/chloroethylene or chlorofluoroethylene of at least about 0.75 at substantially ambient pressure and the reaction allowed to proceed for at least about 3 seconds. Then, the molar ratio of $CH_{4-a-b}Cl_aF_b$/chloroethylene or chlorofluoroethylene will be adjusted to about 2.5 and the pressure increased to about 7 psig, and the reaction allowed to proceed for at least about 5 seconds. Finally, the $CH_{4-a-b}Cl_aF_b$/chloroethylene or chlorofluoroethylene ratio will be adjusted to about 6 and the pressure increased to at least about 35 psig. It is expected that $CH_{4-a-b}Cl_aF_b$ and chloroethylene or chlorofluoroethylene conversions and % selectivity to chlorinated and/or fluorinated propenes will be similar to those expected in connection with Example I, above with the exception that a lesser conversion is expected for $CH_{4-a-b}Cl_aF_b$ with b>0 and a greater conversion is expected for $CH_{4-a-b}Cl_aF_b$ with a>1.

EXAMPLE VI

Impact of the Combination of Lowered Temperature and Increased Pressure on the Production of the Chlorinated and/or Fluorinated Propene A flow of 200 sccm of chloroethylene or chlorofluoroethylene will be established through a glass tube reactor (¾" inner diameter, 40" in length) packed with glass beads having a porosity of 0.35. The initial temperature within the reactor and that of the reactants (mixed at the entrance of the reactor) will be adjusted to achieve isothermal conditions of about 548° C. and the pressure adjusted to be about 7 psig. The flow will be adjusted to provide a molar ratio of $CH_{4-a-b}Cl_aF_b$/chloroethylene or chlorofluoroethylene of about 2.5 and the reaction allowed to proceed for at least about 3 seconds, at which time the temperature will be decreased to about 450° C. and the pressure increased to about 200 psig. The reaction will be allowed to proceed at these conditions for at least about 52 seconds. Then, the temperature will again be decreased to about 400° C. It is expected that $CH_{4-a-b}Cl_aF_b$ and chloroethylene or chlorofluoroethylene conversions and % selectivity to chlorinated and/or fluorinated propenes will be similar to those expected in connection with Example II, above.

EXAMPLE VII

Impact of the Use of an Catalyst/Initiator and Elevated Pressure on the Production of the Chlorinated and/or Fluorinated Propene A flow of 200 sccm of chloroethylene or chlorofluoroethylene will be established through a glass lined tube reactor (¾" inner diameter, 40" in length) packed with glass beads having a porosity of 0.35. The initial temperature within the reactor and that of the reactants (mixed at the entrance of the reactor), will be adjusted to achieve isothermal conditions of about 548° C. and the pressure adjusted to be about 1200 psig. The flow will be adjusted to provide a molar ratio of $CH_{4-a-b}Cl_aF_b$/chloroethylene or chlorofluoroethylene of about 2.5 and to include an amount of an initiator, either $CCl_4$ or $Cl_2$. The reaction will be allowed to proceed for at least about 5.3 minutes, at which time the pressure will be decreased to about 700 psig. The reaction will be allowed to proceed at these conditions for at least about 3.1 minutes. It is expected that $CH_{4-a-b}Cl_aF_b$ and chloroethylene or chlorofluoroethylene conversions and % selectivity to chlorinated and/or fluorinated propenes will be similar to those expected in connection with Example III, above with the exception that a lesser conversion is expected for $CH_{4-a-b}Cl_aF_b$ with b>0 and a greater conversion is expected for $CH_{4-a-b}Cl_aF_b$ with a>1.

EXAMPLE VIII

Impact of the Use of an Initiator, Lowered Temperature, Increased Pressure and Increased $CH_{4-a-b}Cl_aF_b$/Chloroethylene or Chlorofluoroethylene Molar Ratio on the Production of the Chlorinated and/or Fluorinated Propene A flow of 200 sccm of chloroethylene or chlorofluoroethylene will be established through a glass lined tube reactor (¾" inner diameter, 40" in length) packed with glass beads having a porosity of 0.35. Initially, the pressure within the reactor will be ambient and the temperature within the reactor adjusted to achieve isothermal conditions of about 548° C. The flow will be adjusted to provide a molar ratio of $CH_{4-a-b}Cl_aF_b$/chloroethylene or fluorochloroethylene of about 0.75 with no initiator. The reaction will be allowed to proceed under these conditions for at least about 3 seconds. Then, the temperature will be lowered to about 350° C., the pressure increased to about 700 psig, the $CH_{4-a-b}Cl_aF_b$/chloroethylene or fluorochloroethylene molar ratio increased to about 2.5 and $CCl_4$ initiator introduced at a concentration of from about 3000-4000 ppm. The reaction will be allowed to proceed at these conditions for at least about 3.4 minutes. It is expected that $CH_{4-a-b}Cl_aF_b$ and chloroethylene or chlorofluoroethylene conversions and % selectivity to chlorinated and/or fluorinated propenes will be similar to those expected in connection with Example IV, above with the exception that a lesser conversion is expected for $CH_{4-a-b}Cl_aF_b$ with b>0 and a greater conversion is expected for $CH_{4-a-b}Cl_aF_b$ with a>1.

EXAMPLE IX

Impact of the Use of an Initiator, Lowered Temperature, Increased Pressure and Increased Methylene Chloride/Perchloroethylene Molar Ratio on the Fouling Rate in the Production of 1,1,2,3-tetrachloropropene A flow of Perc (383 sccm), MeCl (954 sccm), $CCl_4$ (22 sccm), and nitrogen (2 sccm) is established through a Hastelloy C tube reactor (0.62" inner diameter, 10" in length) with two heated zones. Zone 1 (99 cc) represents the preheat zone and is typically kept at 325° C. and zone 2 (50 cc) is kept at the desired reaction temperature. The effluent is delivered to a room temperature steel vessel (2 L) while maintaining pressure and allowing the nitrogen and hydrogen chloride produced by the reaction to vent to a caustic scrubber. The pressure is slowly reduced on the steel vessel allowing the unreacted methyl chloride to also vent to the scrubber. The remaining liquids are collected, passed through a 1 μm filter, and analyzed by gas chromatography. The pressure within the reactor is adjusted to about 260 psig.

Initially, the temperature within the reaction zone is adjusted to achieve near isothermal conditions of about 470° C. The flow is adjusted to provide a molar ratio of MeCl/Perc of about 2.5 with $CCl_4$ as an initiator at a concentration of 2.3 mole %. At 15 second overall residence time, the initial Perc conversion is about 22%.

A second run with flows of Perc (506 sccm), MeCl (1258 sccm), $CCl_4$ (29 sccm), and nitrogen (2 sccm) is conducted at the same conditions, with a shorter residence time of 11 seconds, to provide a lower initial Perc conversion of about 12%. For a third run, the temperature of the reaction zone is adjusted to 430° C. with flows of Perc (211 sccm), MeCl (528 sccm), CCl$_4$ (12 sccm), and nitrogen (2 sccm) with a residence time of 29 seconds, and provided an initial Perc conversion of about 14%. During the course of the runs the reactor is fouled by the formation of carbonaceous substance as byproducts of the main reaction build up within the reactor wall, in particular towards the end of the reactor where the extent of reaction is the greatest. The impact of the accumulation of the carbonaceous material effectively reduces the reaction volume and results in the reduction in the residence time required to achieve the same perk conversion as obtained initially. The impact of fouling on the Perc conversion with time or cumulative TCPE production normalized to the reactor volume is shown in FIG. 2 for the three operating conditions.

Figure 2:
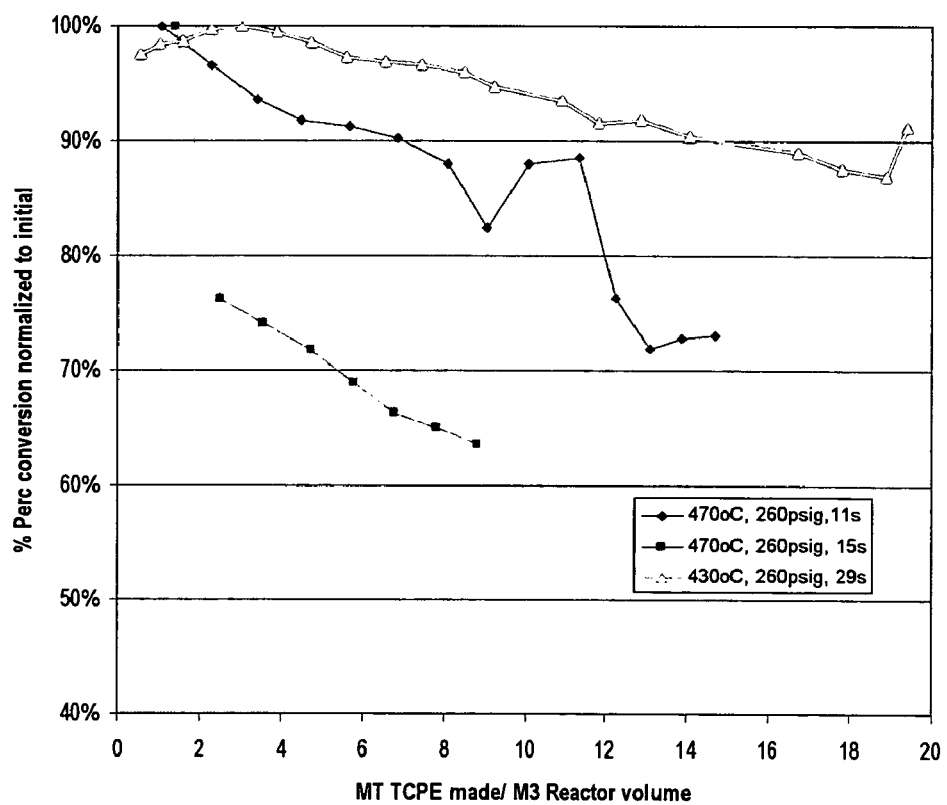
FIG. 2 is a graphical depiction of the impact of fouling on perchloroethylene conversion at various temperatures and 260 psig as a function of cumulative 1,1,2,3-tetrachloropropene production in Metric Ton (MT) normalized to reactor volume in m$^3$.

More specifically, FIG. 2 shows that operating at higher temperatures has a significant impact on the reactor capacity and hence TCPE production. For example, to achieve 10 Metric Ton (MT) TCPE production per 1 m$^3$ of reactor volume, operating at a higher temperature and longer residence time (470° C. and 15 s) can potentially result in about a 40% decline in production, as compared to about a 6% decline in production at an operating temperature of about 430° C. An improvement from the 40% decline to a 20% decline in production can be provided while operating at 470° C. and producing 10 MT TCPE/m$^3$, but this is obtained in the expense of lower initial Perc conversion as compared to the 430° C. operating temperature.

This example thus illustrates that operating at lower temperature reduces the formation of byproducts that foul the reactor and reduce the effective reactor volume over time.

EXAMPLE X

Comparison of Results Provided by the Present Method to Those Provided by Conventional Methods U.S. Pat. No. 3,446,859 teaches that a 5% yield to TCPE can be obtained by reaction of MeCl and Perc, without initiator, at atmospheric pressure, a temperature of about 640° C. and with residence times of 4 seconds and 7 seconds. As disclosed herein, TCPE undergoes significant thermal decomposition at temperatures much lower than 640° C., and indeed, duplication of the conditions taught in the '859 patent shows that the selectivity obtained at these conditions is very poor (Comp 1, Table 5, below). This lower selectivity is likely caused by significant carbon loss to production of byproducts and build-up of the same, as well as other carbonaceous deposits, in the reactor.

In contrast, the same conversion of 13.6% is obtained with pressures of as low as about 345 psia, higher MeCl/Perc ratios, and substantially lower temperatures, e.g., at 430° C. while yet providing a TCPE selectivity of 91%. Even utilizing reaction temperatures much lower than 430° C., with reactor pressures up to 465 psia, conversions of greater than 5% are achieved with TCPE selectivity greater than 94%. The results for this example are summarized in Table 5, below.

COMPARATIVE EXAMPLE 1

Comp 1

The comparative example is carried out according to the procedure described in the '859 patent as follows. Tetrachloroethylene (2.8 moles, 477 g) is fed continuously, at a flow rate of 120 mL per hour, into an empty quartz tube (150 cc) maintained at 630° C. and at atmospheric pressure (15 psia). Simultaneously, methyl chloride (2.2 moles) is fed continuously at a flow rate of 20 liters per hour. The retention time of the reaction mixture is about 3-4 seconds. The reactor effluent is passed through a water cooled condenser (70 cc) and collected in a cold trap (−78° C.). The mixture is warmed to room temperature to allow the produced hydrogen chloride and unreacted methyl chloride to vent to a caustic scrubber. A dark colored crude liquid (440 g) is recovered from the trap and deposited carbonaceous material (3.2 g) removed from the reactor walls.

A representative portion of the crude liquid (205 g) is taken and removal of the solids (1.7 g or 0.81 wt % of crude portion) via vacuum distillation yields a light yellow liquid (203 g) consisting of perk (92 mol %), TCPE (6.2 mol %), and higher boiling components, including but not limited to, the following isomers of TCPE—$C_3H_2Cl_4$, $C_4H_4Cl_4$, $C_5H_2Cl_6$ (hereinafter referred to as "highers") (1.8 mol %) as quantitated by gas chromatography and mole % assay by 1H NMR analysis using 1,2,3,4-tetrachlorobenzene as an internal standard. Elemental analysis of the dark solid reveals principally carbon (90 wt %) with low levels of chlorine (7 wt %).

In total, 477 g of Perc are fed to the reactor and 443.2 g of material is collected and identified as unreacted Perc (401.6 g), TCPE (27.1 g), highers (7.8 g), and coke (6.8). Perc conversion to TCPE and highers is 5.2% and Perc conversion to coke is 8.4% (assuming appropriate stoichiometry to standard carbonaceous materials). Overall perk conversion is 13.6% with 29.6% selectivity to TCPE, 61.9% selectivity to coke, and 8.5% selectivity to highers. Appropriate stoichiometry requires the loss of one molar equivalent of HCl for each mole of Perc converted to TCPE and highers, and two moles of HCl for each mole of coke formed. Thus, 22.8 g of HCl are assumed to have been vented to the scrubber, bringing the total mass balance to 98%.

EXAMPLE XA

A flow of Perc (202 sccm), MeCl (528 sccm), CCl$_4$ (11.5 sccm), and nitrogen (230 sccm) is established through a Hastelloy C tube reactor (0.62" inner diameter, 10" in length) with two heated zones. Zone 1 (99 cc) represents the preheat zone and is typically kept at 325° C. and zone 2 (50 cc) is kept at the 430° C. The effluent is delivered to a room temperature steel vessel (2 L) while maintaining pressure (345 psia) and allowing the nitrogen and hydrogen chloride produced by the reaction to vent to a caustic scrubber. The pressure is slowly reduced on the steel vessel allowing the unreacted methyl chloride to also vent to the scrubber. The remaining liquids are collected, passed through a 1 µm filter, and analyzed by gas chromatography and 1H NMR spectroscopy for quantitation.

Initially, the temperature within the reaction zone is adjusted to achieve near isothermal conditions of about 430° C. The flow is adjusted to provide a molar ratio of MeCl/Perc of about 2.7 with CCl$_4$ as an initiator at a concentration of 1.2 mole %. At 28 second overall residence time, Perc conversion, calculated as (mol % Perc based products/(mol % Perc based products+mol % Perc)), was 13.6%. TCPE selectivity, calculated as (mol % TCPE/mol % Perc based products) was 91.1%.

EXAMPLE XB

A flow of Perc (140 sccm), MeCl (345 sccm), CCl$_4$ (8.4 sccm), and nitrogen (100 sccm) is established through a Hastelloy C tube reactor (0.62" inner diameter, 10" in length) with two heated zones. Zone 1 (99 cc) represents the preheat zone and is typically kept at 325° C. and zone 2 (50 cc) is kept at the 375° C. The effluent is delivered to a room temperature steel vessel (2 L) while maintaining pressure (465 psia) and allowing the nitrogen and hydrogen chloride produced by the reaction to vent to a caustic scrubber. The pressure is slowly reduced on the steel vessel allowing the unreacted methyl chloride to also vent to the scrubber. The remaining liquids are collected, passed through a 1 μm filter, and analyzed by gas chromatography and 1H NMR spectroscopy for quantitation.

Initially, the temperature within the reaction zone is adjusted to achieve near isothermal conditions of about 375° C. The flow is adjusted to provide a molar ratio of MeCl/Perc of about 2.5 with $CCl_4$ as an initiator at a concentration of 1.0 mole %. At 68 second overall residence time, Perc conversion, calculated as (mol % Perc based products/(mol % Perc based products+mol % Perc)), was 4.8%. TCPE selectivity, calculated as (mol % TCPE/mol % Perc based products) was 97.0%.

EXAMPLE XC

A flow of Perc (292 sccm), MeCl (589 sccm), $CCl_4$ (17.6 sccm), and nitrogen (2 sccm) is established through a Hastelloy C tube reactor (0.62" inner diameter, 10" in length) with two heated zones. Zone 1 (99 cc) represents the preheat zone and is typically kept at 325° C. and zone 2 (50 cc) is kept at 395° C. The effluent is delivered to a room temperature steel vessel (2 L) while maintaining pressure (465 psia) and allowing the nitrogen and hydrogen chloride produced by the reaction to vent to a caustic scrubber. The pressure is slowly reduced on the steel vessel allowing the unreacted methyl chloride to also vent to the scrubber. The remaining liquids are collected, passed through a 1 μm filter, and analyzed by gas chromatography and 1H NMR spectroscopy for quantitation.

Initially, the temperature within the reaction zone is adjusted to achieve near isothermal conditions of about 395° C. The flow is adjusted to provide a molar ratio of MeCl/Perc of about 2.0 with $CCl_4$ as an initiator at a concentration of 1.9 mole %. At 44 second overall residence time, Perc conversion, calculated as (mol % Perc based products/(mol % Perc based products+mol % Perc)), was 8.2%. TCPE selectivity, calculated as (mol % TCPE/mol % Perc based products) was 94.1%.

The results from the Comparative Example and Examples XA-XC are summarized in Table 5 below.

EXAMPLE XI

Use of Hexachloroethane, Carbon Tetrachloride, Chlorine, Benzotrichloride, and Hexachloroacetone as Catalysts/Initiators

EXAMPLE XIA

A flow of Perc (163 sccm), MeCl (406 sccm), carbon tetrachloride ($CCl_4$, 9.3 sccm), and nitrogen (190 sccm) is established through a Hastelloy C tube reactor (0.62" inner diameter, 10" in length) with two heated zones. Zone 1 (99 cc) represents the preheat zone and is typically kept at 325° C. and zone 2 (50 cc) is kept at 430° C. The effluent is delivered to a room temperature steel vessel (2 L) while maintaining pressure (275 psia) and allowing the nitrogen and hydrogen chloride produced by the reaction to vent to a caustic scrubber. The pressure is slowly reduced on the steel vessel allowing the unreacted methyl chloride to also vent to the scrubber. The remaining liquids are collected, passed through a 1 μm filter, and analyzed by gas chromatography and 1H NMR spectroscopy for quantitation.

Initially, the temperature within the reaction zone is adjusted to achieve near isothermal conditions of about 430° C. The flow is adjusted to provide a molar ratio of MeCl/Perc of about 2.4 with $CCl_4$ as an initiator at a concentration of 1.2 mole %. At 28 second overall residence time, Perc conversion, calculated as (mol % Perc based products/(mol % Perc based products+mol % Perc)), was 12.8 while TCPE selectivity, calculated as (mol % TCPE/mol % Perc based products) was 92.1%

EXAMPLE XIB

A flow of Perc (161 sccm), MeCl (406 sccm), hexachloroethane ($C_2Cl_6$, 8.5 sccm), and nitrogen (190 sccm) is established through a Hastelloy C tube reactor (0.62" inner diameter, 10" in length) with two heated zones. Zone 1 (99 cc) represents the preheat zone and is typically kept at 325° C. and zone 2 (50 cc) is kept at 430° C. The effluent is delivered to a room temperature steel vessel (2 L) while maintaining pressure (275 psia) and allowing the nitrogen and hydrogen chloride produced by the reaction to vent to a caustic scrubber. The pressure is slowly reduced on the steel vessel allowing the unreacted methyl chloride to also vent to the scrubber.

TABLE 5

| ID | Temp (° C.) | Press (PSIA) | MeCl/Perc | Res time (s) | Catalyst/ Init. | Init. mole % | % Perc conversion | % TCPE selectivity |
|---|---|---|---|---|---|---|---|---|
| Comp1 | 630 | 15 | 0.8 | 4 | none | 0 | 13.6 | 29.6 |
| ExXA | 430 | 345 | 2.7 | 28 | $CCl_4$ | 1.2 | 13.6 | 91.1 |
| ExXB | 375 | 465 | 2.5 | 68 | $CCl_4$ | 1.0 | 4.8 | 97.0 |
| ExXC | 395 | 465 | 2.0 | 44 | $CCl_4$ | 1.9 | 8.2 | 94.1 |

As shown in Table 5, the conversion provided by the conventional method (Comp 1) disclosed in the '859 patent can be attained if higher pressure and initiator is used, however, selectivity is dramatically decreased as compared to Examples XA-XC. Further, Table 5 also shows that temperatures much below the conventional temperature of 630° C., and even below 430° C., can be used to generate commercially reasonable Perc conversions if increased pressure and/or catalyst/initiator is/are used.

The remaining liquids are collected, passed through a 1 μm filter, and analyzed by gas chromatography and 1H NMR spectroscopy for quantitation.

Initially, the temperature within the reaction zone is adjusted to achieve near isothermal conditions of about 430° C. The flow is adjusted to provide a molar ratio of MeCl/Perc of about 2.5 with $C_2Cl_6$ as an initiator at a concentration of 1.1 mole %. At 28 second overall residence time, Perc conversion, calculated as (mol % Perc based products/(mol % Perc based products+mol % Perc)), was 14.8 and TCPE selectivity, calculated as (mol % TCPE/mol % Perc based products) was 90.1%

EXAMPLE XIC

A flow of Perc (137 sccm), MeCl (365 sccm), hexachloroethane ($C_2Cl_6$, 7.2 sccm), and nitrogen (160 sccm) is established through a Hastelloy C tube reactor (0.62" inner diameter, 10" in length) with two heated zones. Zone 1 (99 cc) represents the preheat zone and is typically kept at 325° C. and zone 2 (50 cc) is kept at the 380° C. The effluent is delivered to a room temperature steel vessel (2 L) while maintaining pressure (415 psia) and allowing the nitrogen and hydrogen chloride produced by the reaction to vent to a caustic scrubber. The pressure is slowly reduced on the steel vessel allowing the unreacted methyl chloride to also vent to the scrubber. The remaining liquids are collected, passed through a 1 μm filter, and analyzed by gas chromatography and 1H NMR spectroscopy for quantitation.

Initially, the temperature within the reaction zone is adjusted to achieve near isothermal conditions of about 380° C. The flow is adjusted to provide a molar ratio of MeCl/Perc of about 2.6 with $C_2Cl_6$ as an initiator at a concentration of 1.1 mole %. At 52 second overall residence time, Perc conversion, calculated as (mol % Perc based products/(mol % Perc based products+mol % Perc)), was 4.3 and TCPE selectivity, calculated as (mol % TCPE/mol % Perc based products) was 97.7%.

EXAMPLE XID

A flow of Perc (279 sccm), MeCl (710 sccm), benzotrichloride (BTC, $PhCCl_3$, 7.3 sccm), and nitrogen (2 sccm) is established through a Hastelloy C tube reactor (0.62" inner diameter, 10" in length) with two heated zones. Zone 1 (99 cc) represents the preheat zone and is typically kept at 325° C. and zone 2 (50 cc) is kept at 400° C. The effluent is delivered to a room temperature steel vessel (2 L) while maintaining pressure (345 psia) and allowing the nitrogen and hydrogen chloride produced by the reaction to vent to a caustic scrubber. The pressure is slowly reduced on the steel vessel allowing the unreacted methyl chloride to also vent to the scrubber. The remaining liquids are collected, passed through a 1 μm filter, and analyzed by gas chromatography and 1H NMR spectroscopy for quantitation.

Initially, the temperature within the reaction zone is adjusted to achieve near isothermal conditions of about 400° C. The flow is adjusted to provide a molar ratio of MeCl/Perc of about 2.5 with benzotrichloride as an initiator at a concentration of 0.7 mole %. At 28 second overall residence time, Perc conversion, calculated as (mol % Perc based products/ (mol % Perc based products+mol % Perc)), was 9.3 and TCPE selectivity, calculated as (mol % TCPE/mol % Perc based products) was 94.0%. This shows that about 400° C. reactor temperature can be used with BTC as initiator concentration 345 psig pressure to achieve >9% Perc conversion as compared without initiator and at atmospheric pressure (see Comp1 in Table 6).

EXAMPLE XIE

A flow of Perc (231 sccm), MeCl (568 sccm), hexachloroacetone (HCA, $(Cl_3C)_2C_2CO$ 2.2 sccm), and nitrogen (2 sccm) is established through a Hastelloy C tube reactor (0.62" inner diameter, 10" in length) with two heated zones. Zone 1 (99 cc) represents the preheat zone and is typically kept at 325° C. and zone 2 (50 cc) is kept at 400° C. The effluent is delivered to a room temperature steel vessel (2 L) while maintaining pressure (275 psia) and allowing the nitrogen and hydrogen chloride produced by the reaction to vent to a caustic scrubber. The pressure is slowly reduced on the steel vessel allowing the unreacted methyl chloride to also vent to the scrubber. The remaining liquids are collected, passed through a 1 μm filter, and analyzed by gas chromatography and 1H NMR spectroscopy for quantitation.

Initially, the temperature within the reaction zone is adjusted to achieve near isothermal conditions of about 400° C. The flow is adjusted to provide a molar ratio of MeCl/Perc of about 2.5 with hexachloroacetone as an initiator at a concentration of 0.3 mole %. At 28 second overall residence time, Perc conversion, calculated as (mol % Perc based products/ (mol % Perc based products+mol % Perc)), was 10.9 and TCPE selectivity, calculated as (mol % TCPE/mol % Perc based products) was 92.1%. Again, this shows that about 400° C. reactor temperature can be used with HCA as initiator with 275 psig pressure to achieve >10% Perc conversion as compared to 630° C. temperature required at atmospheric temperature and without the use of initiator (see Comp 1 in Table 6).

The results from this Example are summarized in Table 6, below, along with data from Example 6 above, including data from Comparative Example 1 and Example XC.

TABLE 6

| ID | Temp (° C.) | Press (PSIA) | MeCl/Perc | Res time (s) | Catalyst/ Init. | Init. Mole % | % Perc conv | % TCPE selectivity |
|---|---|---|---|---|---|---|---|---|
| Comp1 | 630 | 15 | 0.8 | 4 | None | 0 | 13.6 | 29.6 |
| Ex. XC | 375 | 465 | 2.5 | 68 | $CCl_4$ | 1.0 | 4.8 | 97.0 |
| ExXIA | 430 | 275 | 2.4 | 28 | $CCl_4$ | 1.2 | 12.8 | 92.1 |
| ExXIB | 430 | 275 | 2.5 | 28 | $C_2Cl_6$ | 1.1 | 14.8 | 90.1 |
| ExXIC | 380 | 415 | 2.6 | 52 | $C_2Cl_6$ | 1.1 | 4.3 | 97.7 |
| ExXID | 400 | 345 | 2.5 | 28 | $PhCCl_3$ | 0.7 | 9.3 | 94.0 |
| ExXIE | 400 | 275 | 2.5 | 28 | $(Cl_3C)_2CO$ | 0.3 | 10.9 | 92.1 |

As shown in Table 6, both carbon tetrachloride and hexachloroethane can provide greater perk conversion and much greater TCPE selectivity than that provided by the conventional method, i.e., with no catalyst/initiator. Further, under the same reaction conditions (temperature, pressure, residence time, initial loading), use of hexachloroethane can provide increased conversions as compared to carbon tetrachloride. Also, the use of benzotrichloride and hexachloroacetone enable further reduction in reaction temperature (400° C.) while maintaining conversions near 10% at lower initiator loadings. TCPE selectivities track according to Perc conversion and are not influenced by the respective initiators.

Figure 3:
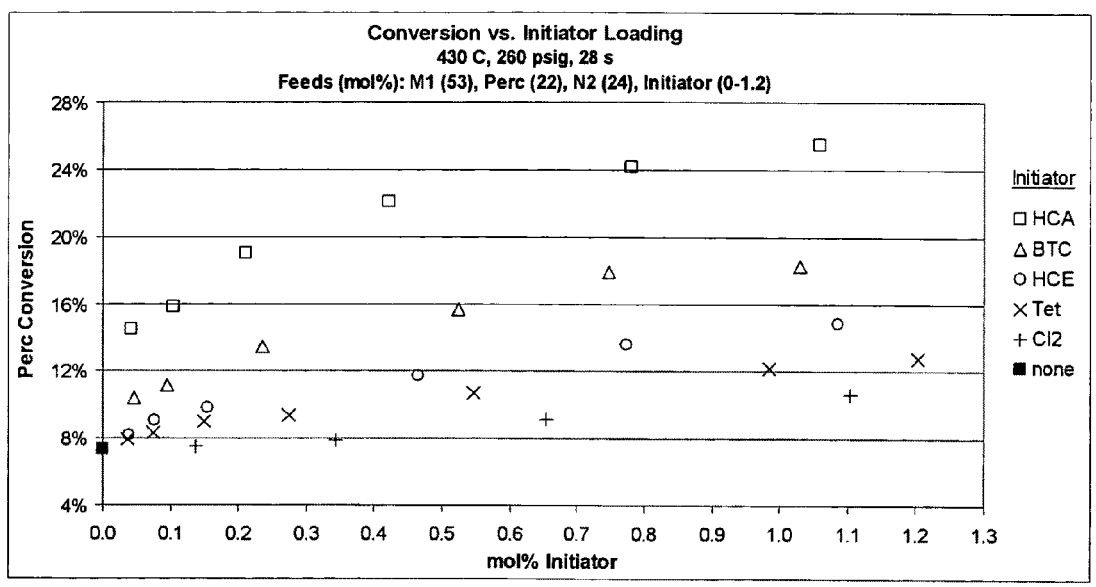
FIG. 3 is a graphical depiction of the impact of the concentration of various catalysts/initiators on perchloroethylene conversion at constant temperature, pressure and residence time.
Figure 4:
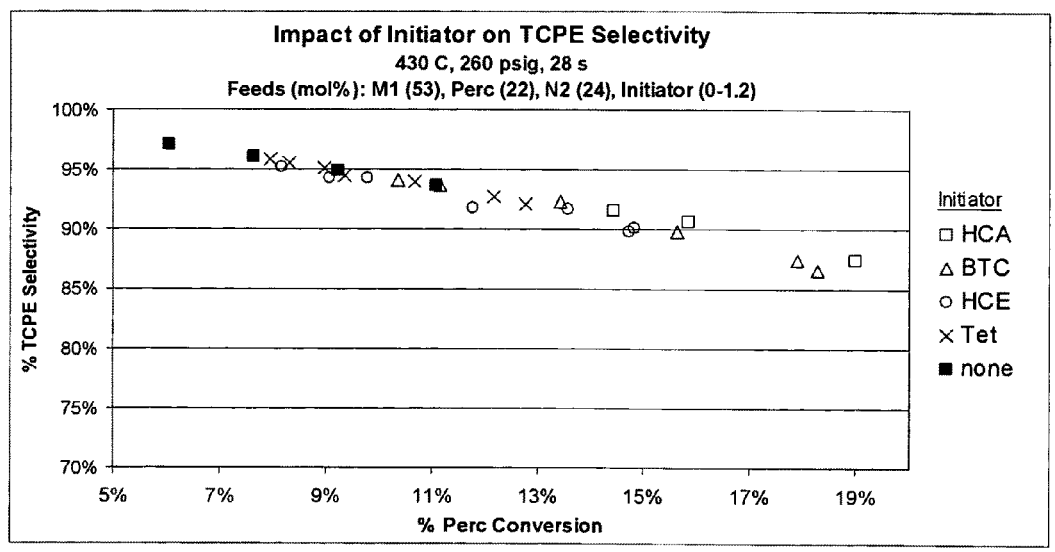
FIG. 4 is a graphical depiction of the impact of various catalysts/initiators on 1,1,2,3-tetrachloropropene selectivity at various perchloroethylene conversions taken at fixed temperature, residence time, and methylene chloride/perchloroethylene ratio.
Figure 5:
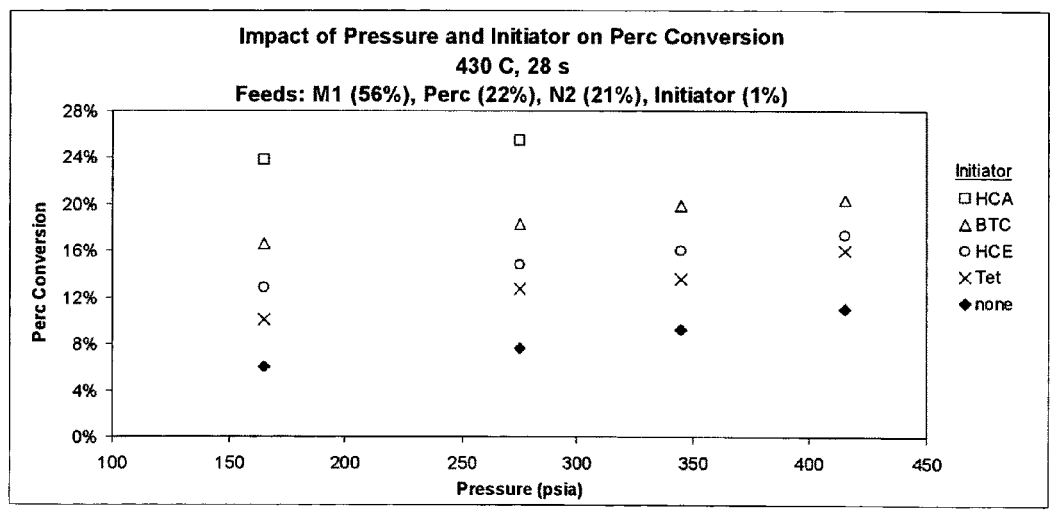
FIG. 5 is a graphical depiction of the impact of higher pressure and various catalysts/initiators on perchloroethylene conversion at constant temperature, pressure catalyst concentration and residence time.

Further results from Example 7 are also shown in FIG. 3. More specifically, and as shown in FIG. 3, when hexachloroethane and carbon tetrachloride are used at increasing concentrations, generally speaking, increasing Perc conversions are seen. Further, use of chlorine under analogous conditions to those described above for hexachloroethane and carbon tetrachloride, shows similar results, i.e., increased Perc conversions with increased concentrations of chlorine. Use of benzotrichloride and hexachloroacetone enable even higher Perc conversions at similar catalyst/initiator loadings. See, FIG. 3. Advantageously, and as shown in FIG. 4, this increased Perc Conversion is not accompanied with a concurrent significant decrease in TCPE selectivity. Finally, FIG. 5 shows that, at higher pressures, all catalyst/initiators (carbon tetrachloride, hexachloroethane, benzotrichloride, and hexachloroacetone) provide higher Perc conversions than when no catalyst/initiator is used.

EXAMPLE XII

The Impact of Using High MeCl/Perc Ratio on Perc Conversion and Selectivity

In the manner described in Examples 6A-C and 7A-C, a flow of Perc (54 sccm) and $CCl_4$ (3 sccm) is established through a Hastelloy C tube reactor (0.62" inner diameter, 10" in length) with two heated zones. A flow of 468 sccm comprising a mixture of MeCl and nitrogen is established with the ratio of MeCl to nitrogen varying from 22:1 to 0.22:1. Zone 1 (99 cc) represents the preheat zone and is typically kept at 325° C. and zone 2 (50 cc) is kept at the 430° C. The effluent is delivered to a room temperature steel vessel (2 L) while maintaining pressure (215 psia) and allowing the nitrogen and hydrogen chloride produced by the reaction to vent to a caustic scrubber. The pressure is slowly reduced on the steel vessel allowing the unreacted methyl chloride to also vent to the scrubber. The remaining liquids are collected, passed through a 1 μm filter, and analyzed by gas chromatography and 1H NMR spectroscopy for quantitation.

Initially, the temperature within the reaction zone is adjusted to achieve near isothermal conditions of about 430° C. The flow is adjusted to provide a molar ratio of MeCl/Perc varying between 8:1 and 1:1 with $CCl_4$ as an initiator at a concentration of 0.6 mole %. At 32 second overall residence time, Perc conversion, calculated as (mol % Perc based products/(mol % Perc based products+mol % Perc)), varied between 7.8 and 10.6% and TCPE selectivity, calculated as (mol % TCPE/mol % Perc based products) was always above 94.3%.

Figure 6:
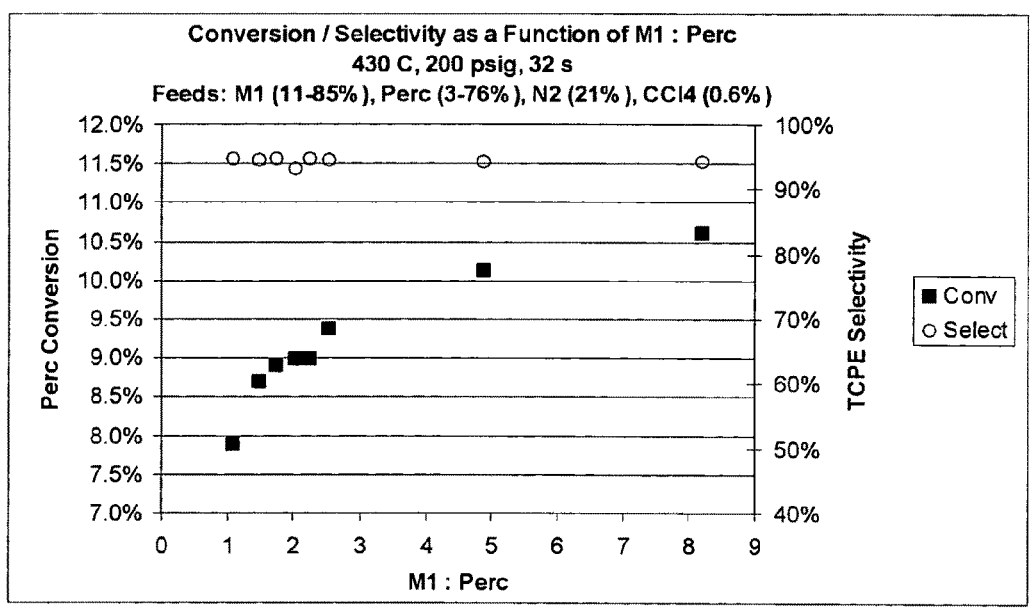
FIG. 6 is a graphical depiction of the impact of methylene chloride/perchloroethylene ratio on perchloroethylene conversion and 1,1,2,3-tetrachloropropene selectivity utilizing the same catalyst/initiator at constant temperature, pressure and residence time and catalyst concentration.

As shown in FIG. 6, high TCPE selectivity is maintained while Perc conversion is increased with the higher MeCl/Perc ratio under the same temperature and pressure conditions and utilizing the same catalyst/initiator. This is in contrast to the lower TCPE selectivity with higher Perc conversion shown in FIG. 5 when MeCl/Perc ratio is fixed, regardless of what catalyst/initiator, if any, is utilized.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A one-step process for the production of chlorinated and/fluorinated propenes comprising:
   Reacting, at elevated pressures, i) a chloroethylene or a chlorofluoroethylene having the formula $CClX\!=\!CX_2$ wherein each X is independently Cl, F and ii) a methane, chloromethane, fluoromethane or chlorofluoromethane having the formula $CH_{4-a-b}Cl_aF_b$ wherein each a and b are 0-3, to provide at least one chlorinated and/or fluorinated propene at a selectivity of at least about 60%.

2. The process of claim 1, wherein the chlorinated and/or fluorinated propene has the formula $CCl_cF_{2-c}\!=\!CCl_dF_{1-d}\!-\!CH_{3-e-f}Cl_eF_f$ wherein c is 0-2, d is 0-1, e is 0-3, and f is 0-3.

3. The process of claim 1, wherein the chloroethylene or chlorofluoroethylene comprises trifluorochloroethylene or perchloroethylene, the fluoromethane comprises methyl fluoride or methyl chloride and the chlorinated and/or fluorinated propene comprises 1,1,2,3-tetrafluoropropene, 1,1,2,3-tetrachloropropene or 1,1,2-chloro,3-fluoropropene.

4. The process of claim 1, wherein the process carried out at a temperature of less than about 450° C.

5. The process of claim 1, wherein the process is carried out at a pressure of greater than about 15 psig.

6. The process of claim 1, wherein the reaction is carried out in the presence of one or more catalysts/initiators comprising carbon tetrachloride, chlorine, hexachloroethane, benzotrichloride, hexachloroacetone or combinations of these.

7. The process of claim 1, wherein the methane, chloromethane, fluoromethane or chlorofluoromethane and the chloroethylene or chlorofluoroethylene are reacted in a ratio of $CH_{4-a-b}Cl_aF_b/CClX\!=\!CX_2$ of greater than or equal to one.

8. The process of claim 1, wherein the pressure is at least about 200 psig and the process is carried out at a temperature of less than about 450° C.

9. The process of claim 1, wherein the pressure is greater than about 15 psig and the process is carried out in the presence of a catalyst/initiator.

10. A process for preparing 2,3,3,3-tetrafluoroprop-1-ene (HFO-1234yf) or 1,3,3,3-tetrafluoroprop-1-ene (HFO-1234ze) comprising converting a chlorinated and/or fluorinated propene prepared by the process of claim 1 into 2,3,3,3-tetrafluoroprop-1-ene (HFO-1234yf) or 1,3,3,3-tetrafluoroprop-1-ene (HFO-1234ze).

* * * * *

UNITED STATES PATENT AND TRADEMARK OFFICE
CERTIFICATE OF CORRECTION

PATENT NO. : 8,258,353 B2  
APPLICATION NO. : 12/799170  
DATED : September 4, 2012  
INVENTOR(S) : William J. Kruper et al.

Page 1 of 1

It is certified that error appears in the above-identified patent and that said Letters Patent is hereby corrected as shown below:

In column 22, line 9, claim 1, "and/fluorinated propenes" should read "and/or fluorinated propenes"

Signed and Sealed this
Eighteenth Day of December, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,258,353 B2 | Page 1 of 1 |
| APPLICATION NO. | : 12/799170 | |
| DATED | : September 4, 2012 | |
| INVENTOR(S) | : William J. Kruper, Jr. et al. | |

It is certified that error appears in the above-identified patent and that said Letters Patent is hereby corrected as shown below:

On the Title page, item number (73), Assignee, "Dow Global Technologies, LLC" should read "Dow Global Technologies LLC"

Signed and Sealed this
Fourteenth Day of October, 2014

Michelle K. Lee
*Deputy Director of the United States Patent and Trademark Office*